(12) United States Patent
Ter-Zakarian

(10) Patent No.: US 7,563,804 B1
(45) Date of Patent: Jul. 21, 2009

(54) FMF TREATMENT

(76) Inventor: Hovanes John Ter-Zakarian, 2332 Flintridge Dr., Glendale, CA (US) 91206

( * ) Notice: Subject to any disclaimer, the term of this patent is extended or adjusted under 35 U.S.C. 154(b) by 487 days.

(21) Appl. No.: 10/826,901

(22) Filed: Apr. 19, 2004

(51) Int. Cl.
*A01N 43/42* (2006.01)
(52) U.S. Cl. .................. 514/311; 514/312; 514/313; 514/314; 514/381
(58) Field of Classification Search ............ None
See application file for complete search history.

(56) References Cited

U.S. PATENT DOCUMENTS 6,797,723 B1 *  9/2004  Sawyer et al. ............ 514/406

2001/0053764 A1 * 12/2001 Sims et al. ............ 514/12

OTHER PUBLICATIONS

Frenkel et al. Increased Urniary E4 . . . 2001.*
PDR 53rd edition 1999.*

* cited by examiner

*Primary Examiner*—Sreeni Padmanabhan
*Assistant Examiner*—Layla Soroush
(74) *Attorney, Agent, or Firm*—William W. Haefliger

(57) ABSTRACT

The method of improving FMF control, in humans, which includes administering, on an average daily basis, between 5 and 15 milligrams of LTRA to a patient suffering from FMF.

4 Claims, No Drawings

FMF TREATMENT

BACKGROUND OF THE INVENTION

This invention relates generally to improvements in treatment control primarily of the disease known s FMF (Familian Mediterranean Fever).

FMF is a widely known disease affecting millions of human beings, and there is consequently great need for effective treatment of humans suffering from FMF.

SUMMARY OF THE INVENTION

It is a major object of the invention to provide effective treatment for FMF, including improvements in FMF control; and in this regard, it has now been discovered that effective control of FMF in humans is achieved by administering, on an average daily basis, between 5 and 15 milligrams of LTRA to a patient suffering from FMF.

Such administering of LTRA is preferably orally, such as in tablet form. As will be seen, it is preferred that about 10 milligrams of LTRA be administered, on an average daily basis, for at least as long as significant FMF conditions are observed in a human being or patient, for example someone between 9 and 72 years of age. It has been discovered that FMF symptoms can thereby be eliminated.

DETAILED DESCRIPTION

As stated, it has been discovered that effective control of FMF in humans is achieved by oral administration of LTRA in the dosages referred to above. FMF is an inherited disorder usually characterized by recurrent episodes of fever and peritonitis (inflammation of the abdominal membrane).

Researchers have identified the gene of FMF and found several different gene mutations that cause this inherited rheumatic disease. The gene, found on chromosome 16, codes for a protein that is found particularly in granulocytes—which are white blood cells associated with the immune response. That protein is believed to assist in keeping inflammation under control by deactivating the immune response. Otherwise, a full-blown inflammatory reaction occurs; i.e. an attack of FMF.

FMF sufferers undergo bouts of fever, typically with severe abdominal pain associated with inflammation of the abdominal cavity (peritonitis). Attacks can also include arthritis, skin rashes, and chest pain from inflammation of the lung cavity. Certain patients develop amyloidosis, a potentially deadly accumulation of protein in vital organs such as the kidneys.

The only present treatment for FMF is a drug, known as colchicine, which patients need to take every day, for life, and which causes side effects such as diarrhea and abdominal cramps.

FMF occurs most commonly in people of non-Ashkenzi Jewish, Armenian, Arab and Turkish background living in the United States and abroad. As many as 1 in 200 people in these populations have the disease, and as many as one in five to one in seven carry a mutated FMF gene. A person must inherit two mutated copies of the gene—one from each parent—in order to acquire FMF.

LTRA as referred to above is the acronym for leukotriene receptor antagonists, which block substances in the body known as leukotrienes. The latter are derived from the action of enzyme 5-lipoxygenase on arachidonic acid, and are chemicals which cause asthma symptoms.

One synthetic LTRA is known as ZAFIRLUKAST with the chemical name of 4-5-cyclopentyloxy-carbonylamino-1-methyl-indol-3-ylmethyl-3-methoxy-N-o-tonylsulfanylbenzamide.

Another synthetic LTRA is known as SINGULAIR, a product of Merck & Co., Whitehouse Station, N.J. Montelukant sodium, the active ingredient in SINGULAIR, has the formula $C_{35}H_{35}$ ClNNa $0_3$S.

The preferred method of improving FMF control in humans, or of treating FMF sufferers, includes administering on an average daily basis, between 5 and 15 milligrams of LTRA to a patient suffering from FMF. Such LTRA is preferably administrated orally, as in tablet form, and daily, for as long as FMF symptoms persist. Preferably about 10 milligrams of LTRA is administered, on a daily basis, to humans between 9 and 72 years of age. Such tablets may consists of the product known as ZAFIRLUCAST, or the Merck & Co., Inc. product known as SINGULAIR.

TEST RESULTS

Over 20 patients were treated as described above, for periods of time varying from 5 months to 2½ years, i.e. until FMF symptoms (fever, acute attacks, etc) were no longer detected, in all cases. LTRA dosages were approximately 10 milligrams daily, in tablet form.

I claim:

1. The method of treating Familian Mediterranean Fever (FMF) in a human suffering from FMF, which consists of orally administering, on an average daily basis, between 5 and 15 milligrams of leukotriene receptor antagonist (LTRA) selected from the group consisting of 4-5-cyclopentyloxy-carbonylamino-1-methyl-indol-3-ylmethyl-3-methoxy-N-o-tonylsulfanylbenzamide and montelukant sodium to said patient and continuing said administration at said milligram level, and said average daily basis level as long as the FMF symptoms continue.

2. The method of claim 1 wherein said LTRA is administrated orally in tablet form, wherein about 10 milligrams of said LTRA is administered, on a daily basis, for periods of time varying from 5 months to 2½ years and wherein said LTRA consists of 4-5-cyclopentyloxy-carbonylamino-1-methyl-indol-3-ylmethyl-3-methoxy-N-o-tonylsulfanylbenzamide tablets.

3. The method of claim 1 wherein said LTRA is administered orally in tablet form, wherein about 10 milligrams of said LTRA is administered, on a daily basis, for periods of time varying from 5 months to 2½ years and wherein said LTRA consists of montelukant sodium tablets.

4. The method of claim 1 wherein said human is between 9 and 72 years old.

* * * * *